United States Patent [19]

Welch et al.

[11] 4,001,341

[45] Jan. 4, 1977

[54] EXTRACTION SEPARATION

[75] Inventors: John F. Welch; Frank P. Civardi, both of Pittsfield, Mass.

[73] Assignee: General Electric Company, Pittsfield, Mass.

[22] Filed: Jan. 24, 1964

[21] Appl. No.: 340,101

[52] U.S. Cl. .......................................... 260/621 B
[51] Int. Cl.$^2$ ....................................... C07C 37/28
[58] Field of Search ............ 260/621 B, 627 G, 627

[56] References Cited

UNITED STATES PATENTS 2,581,406   1/1952   Golumbic et al. ................. 260/627

OTHER PUBLICATIONS

Walker, "Industrial and Chemical Engineering," vol. 42, No. 6, pp. 1226–1230 [1950].
Golumbic et al., "Jour. Am. Chem. Soc.," vol. 71, pp. 2624–2627, [1949].

*Primary Examiner*—Norman Morgenstern
*Attorney, Agent, or Firm*—William F. Mufatti; Granville M. Pine; Edward A. Hedman

EXEMPLARY CLAIM

1. A process for purifying, in a countercurrent extraction system, a crude 2,6-xylenol feed of 20 to 98% by weight initial purity containing phenolic impurities consisting essentially of phenol and cresols comprising introduction of aqueous inorganic alkali countercurrently to a phenolic impurity-solvent hydrocarbon phase and said crude 2,6-xylenol feed, said aqueous inorganic alkali being introduced at the top of a countercurrent extraction rectifier, said phenolic inpurity-solvent hydrocarbon phase being introduced at the bottom of said countercurrent rectifier, and said crude 2,6-xylenol feed being introduced at a point intermediate thereto, whereby a substantially pure 2,6-xylenol-solvent hydrocarbon stream is removed from the top of the countercurrent extraction rectifier and a first aqueous phase stream is removed from the bottom of the countercurrent extraction rectifier consisting essentially of an aqueous solution of the inorganic alkali salts of the phenolic impurities and a minor portion of the 2,6-xylenol, recovering said portion of the 2,6-xylenol from its aqueous alkali salt solution by contacting it countercurrently with a phenolic impurity-solvent hydrocarbon phase in a stripping zone whereby the first aqueous phase is introduced into the top of said stripping zone and the phenolic impurity-solvent hydrocarbon phase is introduced at the bottom of said stripping zone whereby a phenolic impurity-solvent hydrocarbon-2,6-xylenol stream is recovered from the top of the stripping zone and a portion recycled to the crude 2,6-xylenol feed into the countercurrent extraction rectifier, and a second aqueous phase stream is removed from the bottom of the stripping zone consisting essentially of an aqueous solution of the inorganic alkali salts of the phenolic impurities essentially free of 2,6-xylenol, springing the phenolic salts by addition of acid thereto, recovering the free phenolic impurities essentially free of 2,6-xylenol by extraction from the acidified second aqueous stream with a solvent hydrocarbon to form a phenolic immpurity-solvent hydrocarbon phase and recycling a portion of said phenolic impurity-solvent hydrocarbon phase essentially free of 2,6-xylenol to the bottom of the stripping zone for recovery of the 2,6-xylenol from its aqueous inorganic alkali salt solution.

11 Claims, 1 Drawing Figure

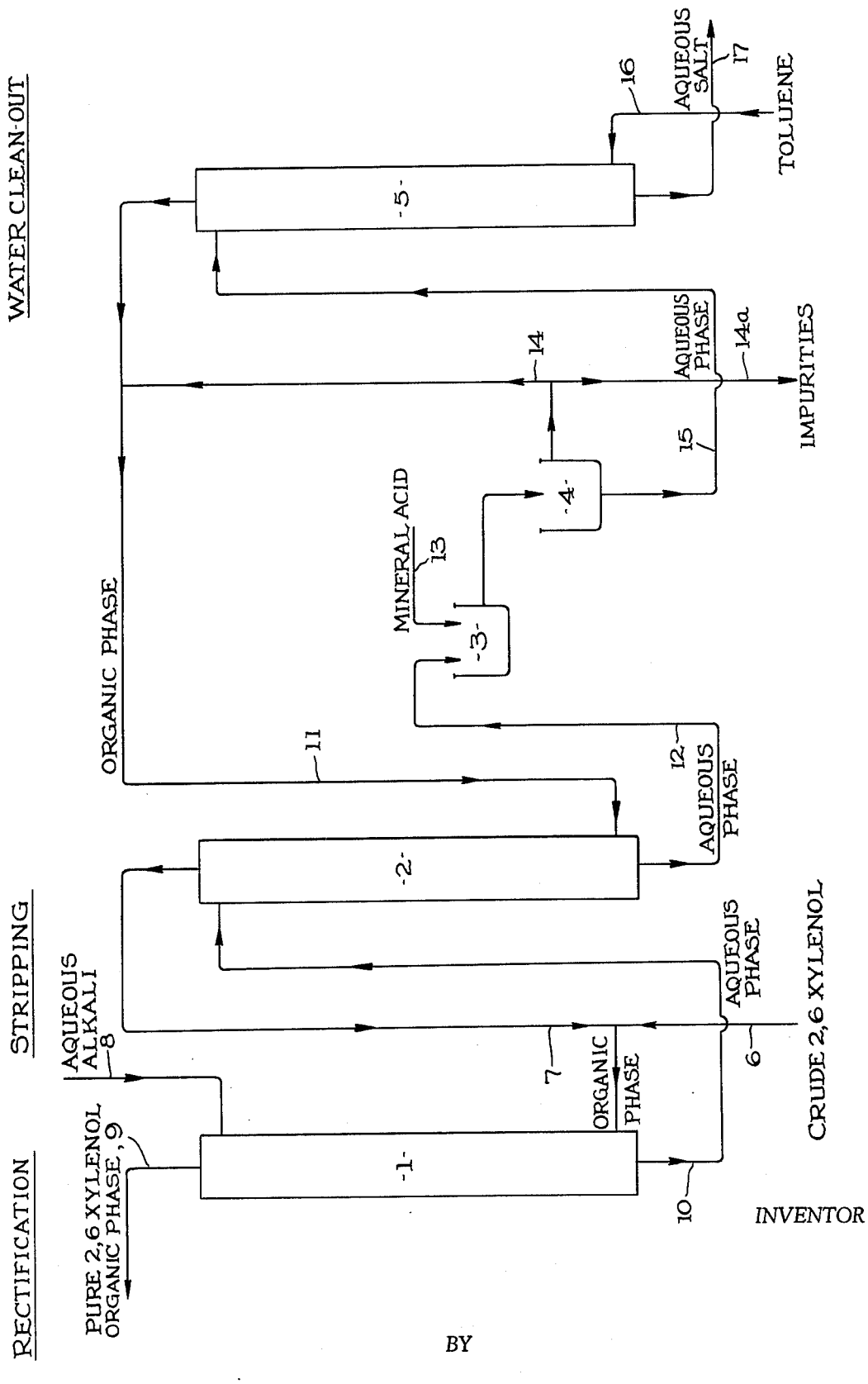

EXTRACTION SEPARATION

This invention relates to a process for the purification of crude 2,6-xylenol by removal of phenolic impurities therefrom through liquid-liquid extraction. More particularly, the present invention relates to a process useful in purifying a crude 2,6-xylenol feed which comprises the countercurrent extraction thereof in a phenolic solvent hydrocarbon phase introduced countercurrently to an aqueous inorganic alkali in a countercurrent extraction system, the extracted phenolic impurities in the aqueous inorganic alkali being recovered and re-cycled in the aforesaid phenolic solvent hydrocarbon phase thus providing in continuous operation a steady state reflux of phenolic impurities in the system from which substantially pure 2,6-xylenol in hydrocarbon solution is then recovered.

Crude 2,6-xylenol is available commercially as an article of commerce in ranges of purity extending from 20% to 98%. The crude product most frequently represents a narrow distillate cut derived from the destructive distillation of coal. Further sources include coke oven tars, petroleum cresylics, oil shale distillates, disproportionation of other phenols, and the like.

2,6-xylenol is necessary in the production of certain synthetic resins and is otherwise useful as an intermediate in the chemical industry and as an anti-oxidant. It is, however, difficult to obtain a highly purified 2,6-xylenol through an economically feasible large scale continuous operation. Since commercial crude 2,6-xylenol is, in itself, a distillation product, a further purification by fractional distillation would require the separation of 2,6-xylenol from a number of other phenols having boiling points closely similar thereto, particularly other xylenol isomers and meta and para cresol. An effective distillation procedure is thus not economically practicable, particularly at the level of availability of the 2,6-xylenol from such present commercial sources. Fractional crystallization, while remaining a useful laboratory technique, is also economically disadvantageous in that, like distillation, commercial production would require high capital investment and utility costs. While double solvent extractive procedures are economically attractive, the prior art does not offer in any such procedure a truly satisfactory yield or purity of product.

In this prior art, as represented by Neuworth in U.S. Pat. No. 2,789,146, the yield is less than 70% and the maximum purity obtained in the final product was 91.2%, which is not substantially pure within the meaning of this specification. According to Neuworth, the product of his double solvent extraction, using a hydrocarbon-aqueous methanol system, must be fractionally crystallized to yield 2,6-xylenol of a higher purity.

According to the present invention, in one of its broader aspects it has been discovered that substantially pure 2,6-xylenol in high yield may be recovered from a crude feed by continuous countercurrent liquid-liquid extraction thereof using as the extracting phase an aqueous inorganic alkaline solution and as the solvent phase a phenolic solvent hydrocarbon. The product is thus recovered in hydrocarbon solution. It is a further discovery of this invention that the efficiency of this countercurrent extraction is considerably enhanced by specific modes of reflux of phenolic impurities. By a mode preferred for a lower volume use this reflux is effected by separation of phenolic solvent impurities from the aqueous alkaline extract thereof, preferably by acidification and decantation, the separated phenols then being re-cycled by introduction into the phenolic solvent hydrocarbon phase. In this double solvent extraction, an aqueous inorganic alkali, preferably a mineral alkali, is fed into the top of a countercurrent extraction system, the phenolic solvent hydrocarbon is fed into the bottom of the system, and the crude 2,6-xylenol feed is introduced into the center thereof. The product in hydrocarbon solution is removed from the top of the system.

The aforementioned extractive system may comprise a rectification zone and a stripping zone. Each zone may be located in a single extracting unit or may represent, respectively, at least one or more extracting units in series. The number and design of the extracting units will generally be determined by the volume and purity level of the feed and the appropriate selection of specific equipment will be readily apparent to those skilled in the art. One consideration, for example, is the higher hold-up required to attain equilibrium, and yield a substantially pure product, when the 2,6-xylenol content of the feed is relatively low. For lower volume use a single extracting unit may be used as, for example, a center feed countercurrent extractor, the upper portion of which serves as a rectification zone, and the lower portion as a stripping zone. Such a system will furnish a high separation efficiency for smaller volumes at a relatively low investment. Where a higher volume feed is processed the rectification and stripping zones may represent two or more extracting units in series. In every instance, however, this invention contemplates the particular selection of convenient equipment or plant design providing the greatest economy of operation with respect to volume and/or purity level of feed, material balance during continuous operation, and the costs of the materials consumed.

In one mode of practice of this invention, crude 2,6-xylenol feed is introduced into the bottom of the rectification zone, or into the center of a center feed column, while aqueous inorganic alkali is introduced at the top. From the bottom of the rectification zone a first aqueous alkaline extract of phenolic impurities is passed into the top of a stripping zone which may be the lower half of a single extracting unit, or at least one separate unit. The phenolic solvent hydrocarbon is introduced at the bottom of the stripping zone and from the top of that zone passes into the bottom of the rectification zone. From the bottom of the stripping zone a second aqueous alkaline extract of phenolic impurities is removed and the extracted phenols contained therein are recovered with a portion thereof being re-cycled by introduction into the bottom of the stripping zone. For lower volume use, recovery of the extracted phenols is most conveniently effected by neutralization of the second aqueous alkaline extract with acid which may conveniently be aqueous acid. The extracted phenols are then recovered by decantation and may be re-cycled with phenolic solvent hydrocarbon fed into the bottom of the stripping zone. Following decantation the aqueous neutral salt solution remaining may be further treated by counter-current extraction with input phenolic solvent hydrocarbon which is then passed into the stripping zone and the aqueous salt solution discharged containing only trace amounts of phenolic impurities.

The crude 2,6-xylenol feed should be substantially phenolic in composition. The principal phenolic impurities present in commercial crudes are meta and para cresols. Other contaminating phenols which may be present, depending upon the source of the crude, are phenol, ortho cresol, xylenol isomers, ethylphenols, etc. The effectiveness of the present process is independent of the presence of these and other naturally occurring phenols present in crude 2,6-xylenol. Phenolic impurities, as defined in this specification, thus include any or all of the phenols discussed above as present in a particular crude feed stock. The process of this invention is substantially unaffected by minor amounts of tar bases, sulfur compounds neutral oils, or the like in the crude feed. However, it should be substantially free of ingredients reactive with the products sought or of other antagonistic material which may hinder or prevent phase separation such as soaps or emulsifying agents. The crude feed may be fed into the system in a solution of the particular organic solvent employed.

The aqueous alkali may comprise a solution of an inorganic base which is hydrocarbon insoluble. The pH of the inorganic alkaline solution should be, of course, more then 7, and preferably within the range of pH 10 through pH 12. It is thus preferable that the aqueous inorganic alkali be approximately one normal and in general not substantially in excess of two normal since the efficiency of the process tends to fall off in excess of that value. The preferred inorganic alkaline solution is a solution of a mineral alkali exemplified by sodium hydroxide, potassium hydroxide, calcium hydroxide, and barium hydroxide. In the preferred embodiment of this invention the aqueous mineral alkali used is 1 normal sodium hydroxide. In another embodiment of this invention the inorganic alkali may comprise aqueous ammonia.

The acid "springing" of the phenols, wherein they are recovered by decantation may be effected by any of the conventionally utilized mineral acids including sulfuric acid and carbon dioxide. In the preferred embodiment of this invention 66° Be sulfuric acid is used.

The phenolic solvent hydrocarbon may be chosen from virtually any of the hydrocarbon solvents, or mixtures thereof, having a good solvation for phenols and preferably being liquid at ambient temperatures and of a density less than the aqueous phase of this process. Among satisfactory solvents are the lower molecular weight cyclic hydrocarbons as exemplified by toluene, benzene, and cyclohexane with toluene being employed in the preferred embodiment of this invention. The recycle procedures of the present invention can be used advantageously in this connection in maintaining or increasing the density of the aqueous phase relative to that of the phenolic solvent hydrocarbon and thus permit the use of higher molecular weight hydrocarbons.

The process of this invention in one of its preferred embodiments is further described and discussed below with reference to the accompanying drawing. The described embodiment is preferred in raising the concentration of 2,6-xylenol in a feed having an initial purity of 20% to 98% to a value above 99%.

In the drawing there is shown a system comprising a rectification zone 1, a stripping zone 2, a mixing tank 3, a decanting tank 4 and a "clean-up" extractor 5. In this preferred embodiment each of the vertical extracting columns 1, 2 and 5 is a countercurrent, multi-stage liquid-liquid extractor. It should be pointed out that a variety of equipment may be used to carry out this invention including any of the commercial countercurrent extractors. It is possible for extractors 1 and 2 to be, respectively, the rectification and stripping zones of a single continuous countercurrent, double solvent, center feed extraction column. The design of any particular column should be determined by the necessity of providing a sufficient number of theoretical extraction stages to efficiently effect the desired extractive procedure performed. Alternative configurations include a conventional packed tower, a pierced plate column, a bubble plate column, a column containing alternate zones of quiescence and turbulence, a series of mixing and decanting tanks, etc. However, in the preferred embodiment each of the extracting columns is a York-Scheibel baffle type extractor with a variable speed drive. For increasing the 2,6-xylenol content of a solution from 50% to over 99%, a 36 stage extractor is preferred. The separatory train, shown as units 3 and 4, may comprise a variety of apparatus including mixing and decanting container as well as other separatory means, such as a distillation assembly, fractional crystallization units etc., to provide extract phenols for re-cyling into the system.

In operation, a crude 2,6-xylenol feed 6 is fed into rectification zone 1 with toluene re-cycle stream 7. In this description the crude comprises 50% 2,6-xylenol, 8% combined phenol and ortho cresol, 40% combined meta and para cresol and 2% other phenolic impurities. The system may be operated with feeds of greater or less 2,6-xylenol content corresponding to the range of commercially available crudes. Optionally, although with somewhat lower efficiency, the crude feed may be introduced in toluene solution. The re-cycle phase in this illustration comprises a toluene solution of re-cycled phenols in substantially the same proportion as feed 6 and passing from the top of stripping zone 2 into the bottom of rectification zone 1. Aqueous alkali feed 8 is introduced at the top of column 1, in this illustration, as a 1 normal sodium hydroxide solution. The organic phase flows upward in rectification zone 1 where it is in intimate, continuous stage-wise contact with the aqueous caustic. Impurities accumulate in the aqueous phase while the crude is purified to 99.9% 2,6-xylenol, with the level of obtainable purity being above 99.99%. From the top of column 1 there is removed raffinate 9 which is substantially pure 2,6-xylenol in toluene solution. A purity in excess of 99% is substantially pure within the meaning of this specification.

From the bottom of rectification column 1 there is removed a first aqueous caustic extract 10 which passes into the top of stripping column 2. First aqueous extract 10 comprises 2,6-xylenol in an approximately 30% ratio to combined phenol, cresols, and xylenols. In stripping column 2 the first aqueous extract 10 is subject to continuous stage-wise countercurrent extraction with re-cycle toluene feed 11 introduced at the bottom of stripping zone 2. In this zone 2,6-xylenol is preferentially stripped from the aqueous phase and returned in solvent re-cycle stream 7 to rectification zone 1. There is removed from the bottom of column 2 a second aqueous caustic extract 12. This second aqueous caustic extract comprises in this illustration 2,6-xylenol in less than 0.5% ratio to combined phenols, cresols and xylenols. The phenols contained in the re-cycle stream 11 passing from the top of "clean-up" extractor 5 into the bottom of stripping unit 2 are in substantially the same ratio as the second aqueous caustic extract 12.

In mixing tank 3 the extracted phenols in extract 12 are "sprung" by 66° Be sulfuric acid introduced at 13. In decanting tank 4 the "sprung" phenols are decanted and returned 14 in re-cycle stream 11. As shown, 14a, a portion of decanted extract phenols may be discarded, or passed to storage. During start-up, and until equilibrium is reached, the re-cycle rate is preferably 100%. During continuous operation, at equilibrium, material balance is maintained and the extract phenols removed at 14a will substantially equal input phenolic impurities. The yield of 2,6-xylenol is thus nearly quantitative and more than 99% of the 2,6-xylenol fed can be recovered.

Aqueous salt solution 15 removed from the separatory train 3 and 4 comprises substantially 1 normal sodium sulfate with traces of phenols, cresols and xylenols. Aqueous salt solution 15 passes into the top of "clean-up" extractor 5 where it is washed countercurrently with input toluene 16 introduced at the bottom of column 5. Washed aqueous salt solution 17, discharged from the bottom of column 5, contains less than 25 parts per million phenol. The phenolic concentration of discharge solution 17 is conveniently controlled through regulation of toluene input 16. From the top of column 5 there is removed toluene re-cycle stream 11 into which the extract phenols are re-cycled.

Extracting columns 1, 2 and 5 may be operated so that the continuous phases therein are either organic or aqueous. It has, however, been found that it is preferable for the most efficient operation of this invention, as illustrated in the present description, for the continuous phase in rectification column 1 to be toluene and the continuous phase in stripping column 2 to be aqueous caustic.

The following examples are further illustrative of the practice of this invention.

EXAMPLE 1

The series of experiments hereindescribed were performed in step-wise approximation of the above-described continuous process in order to quantitatively determine optimum process conditions.

I A

Into a 36 stage York-Scheibel rectification extractor corresponding to rectification extractor 1 of the drawing, there was at the bottom introduced a feed consisting of four volumes of toluene and one volume of a 2,6-xylenol crude comprising 55% 2,6-xylenol, 10.5% combined phenol and ortho cresol and 34.5% combined meta and para cresol. The feed rate was three liters per hour. At the top of the column 1 normal sodium hydroxide was fed at a rate of 3.9 liters per hour. The continuous phase in the extractor was toluene. Agitation speed was 600 rpm. The raffinate phase removed was analyzed at 99.5% 2,6-xylenol and less than 0.5% combined meta and para cresol at 10% concentration. The aqueous caustic extract removed from the bottom of the column was analyzed and the phenolic content consisted of 30% 2,6-xylenol, 20% phenol and 50% combined meta and para cresol. When the experiment was repeated using an aqueous continuous phase, the raffinate was analyzed at 99.0% 2,6-xylenol and 1.0% combined meta and para cresol at 10% concentration. Increase of the caustic flow to a higher rate was found to reduce the percentage concentration in the raffinate but not significantly to affect the purity thereof.

I B

In this experiment, an aqueous phenolic caustic solution, as might be derived from a rectification column as described in IA was introduced at the top of a 36 stage York-Scheibel extractor corresponding to unit 2 of the drawing. The input at the top of the column was a 10% caustic solution of phenols including 39.7% 2,6-xylenol, 16.3% combined phenol and ortho cresol and 44% combined metal and para cresol. The feed rate for the caustic solution was 2 liters per hour. At the bottom of the column toluene was fed at a rate of 1 liter per hour. The raffinate from the top of the column was removed and with respect to its phenolic content analyzed 47% 2,6-xylenol, 16% combined phenol and ortho cresol and 37% combined meta and para cresol. The aqueous extract removed from the bottom of the column was treated with sulfuric acid and the sprung extract phenols decanted. The separated extract phenols analyzed at 0.5% 2,6-xylenol, 22% combined phenol and ortho cresol and 77.5% combined meta and para cresol. About 50% of the separated extract phenols were re-cycled in the toluene feed and the remaining 50% discarded at a rate of approximately 50 grams per hour.

I C

This experiment was to determine the stripping of phenols from the neutralized aqueous salt solution remaining from the decantation described above in IB. The aqueous salt solution from the previous run was fed at a rate of 4.2 liters per hour into the top of a 36 stage extractor corresponding to unit 5 of the drawing. Toluene was fed into the bottom of the extractor at the rate of 1.8 liters per hour. Analysis of the raffinate removed from the top of the column showed that the phenolic content included 4% 2,6-xylenol, 23% phenol and 73% combined meta and para cresol. The extracted aqueous salt solution contained 200 parts per million phenol and cresols. In this run the toluene to aqueous salt ratio was 0.43. At a toluene to aqueous salt solution ratio of one the phenolic contamination in the discarded aqueous salt solution can be reduced to below 25 parts per million.

As a step-wise recapitulation of the process of this invention Examples IA, IB and IC convincingly demonstrate the advantages thereof including a substantially pure product in virtually quantitative yield, and a discard aqueous solution containing only trace amounts of phenols.

EXAMPLE 2

In this example there was used a York-Scheibel 36 stage extractor adapted for center feed. The top half of the column is a rectification zone corresponding to unit 1 of the drawing and the bottom half of the column is a stripping zone corresponding to unit 2 of the drawing. The center feed consisted of four volumes of toluene and one volume of a 2,6-xylenol crude comprising 97% 2,6-xylenol, 1.8% combined phenol and ortho cresol, 0.5% combined meta and para cresol and 0.7% para ethylphenol. The feed rate was 3.6 liters per hour. Into the top of the column 1 normal sodium hydroxide was introduced at a rate of 3.6 liters per hour and at the bottom of the column toluene was fed at a rate of 3.6 liters per hour. The continuous phase was toluene and the column was agitated at 750 rpm. The extract removed from the bottom of the column was decanted following sulfuric acid treatment as described above, and the separated extract phenols re-cycled at a rate of 100%. The column was operated under these conditions for 13 hours and demonstrated continuous operability. The raffinate removed from the top of the column analyzed at 99.9% 2,6-xylenol at 11% concentration, and recovery was substantially quantitative.

EXAMPLE 3

In substantially the same apparatus as Example 2 there was introduced a feed consisting of 1 volume of toluene and 1 volume of crude comprising 89.5% 2,6-xylenol, 1.5% combined phenol and ortho cresol, 9.0% combined meta and para cresol and traces of other phenols. The flow rate was 0.6 liters per hour. At the top of the column 1 normal sodium hydroxide was introduced at a rate of 2.4 liters per hour. At the bottom of the column toluene was introduced at a rate of 3 liters per hour. The continuous phase was toluene and the agitation speed 900 rpm. The aqueous phenolic extract removed from the bottom of the column was treated comparably to that of Example 2. The decanted phenols, which by analysis comprised 60% 2,6xylenol, 5% phenol and ortho cresol, and 35% meta and para cresol, were re-cycled at a rate of 70%. The raffinate removed from the top of the column analyzed at 99.92% 2,6-xylenol at 11% concentration. This test has been carried out for a total of 24 hours continuous operation.

EXAMPLE 4

This experiment was identical with Example 3 except that the decanted phenols were re-cycled at a rate of 80%. The raffinate analyzed at 99.89% 2,6-xylenol.

We claim:

1. A process for purifying, in a countercurrent extraction system, a crude 2,6-xylenol feed of 20 to 98% by weight initial purity containing phenolic impurities consisting essentially of phenol and cresols comprising introduction of aqueous inorganic alkali countercurrently to a phenolic impurity-solvent hydrocarbon phase and said crude 2,6-xylenol feed, said aqueous inorganic alkali being introduced at the top of a countercurrent extraction rectifier, said phenolic impurity-solvent hydrocarbon phase being introduced at the bottom of said countercurrent rectifier, and said crude 2,6-xylenol feed being introduced at a point intermediate thereto, whereby a substantially pure 2,6-xylenol-solvent hydrocarbon stream is removed from the top of the countercurrent extraction rectifier and a first aqueous phase stream is removed from the bottom of the countercurrent extraction rectifier consisting essentially of an aqueous solution of the inorganic alkali salts of the phenolic impurities and a minor portion of the 2,6-xylenol, recovering said portion of the 2,6-xylenol from its aqueous alkali salt solution by contacting it countercurrently with a phenolic impurity-solvent hydrocarbon phase in a stripping zone whereby the first aqueous phase is introduced into the top of said stripping zone and the phenolic impurity-solvent hydrocarbon phase is introduced at the bottom of said stripping zone whereby a phenolic impurity-solvent hydrocarbon-2,6-xylenol stream is recovered from the top of the stripping zone and a portion recycled to the crude 2,6-xylenol feed into the countercurrent extraction rectifier, and a second aqueous phase stream is removed from the bottom of the stripping zone consisting essentially of an aqueous solution of the inorganic alkali salts of the phenolic impurities essentially free of 2,6-xylenol, springing the phenolic salts by addition of acid thereto, recovering the free phenolic impurities essentially free of 2,6-xylenol by extraction from the acidified second aqueous stream with a solvent hydrocarbon to form a phenolic impurity-solvent hydrocarbon phase and recycling a portion of said phenolic impurity-solvent hydrocarbon phase essentially free of 2,6-xylenol to the bottom of the stripping zone for recovery of the 2,6-xylenol from its aqueous inorganic alkali salt solution.

2. The process of claim 1 wherein the aqueous salt solution removed from the bottom of the stripper contains only trace amounts of said phenolic impurities.

3. The process of claim 2 wherein said phenolic solvent hydrocarbon phase is a phenolic solvent cyclic hydrocarbon phase.

4. The process of claim 3 wherein said cyclic hydrocarbon is toluene.

5. The process of claim 3 wherein said cyclic hydrocarbon is benzene.

6. The process of claim 3 wherein said cyclic hydrocarbon is cyclohexane.

7. The process of claim 2 wherein said aqueous inorganic alkali has a pH of at least seven and a normality not substantially greater than 2.

8. The process of claim 7 wherein said aqueous inorganic alkali has a pH of 10 through 12.

9. The process of claim 7 wherein said aqueous inorganic alkali is substantially one normal sodium hydroxide.

10. The process of claim 9 wherein said aqueous acid is substantially 66° Be sulfuric acid.

11. The process of claim 2 wherein said crude 2,6-xylenol feed is in phenolic solvent hydrocarbon solution.

* * * * *